US010688057B2

(12) United States Patent
Boyd et al.

(10) Patent No.: US 10,688,057 B2
(45) Date of Patent: *Jun. 23, 2020

(54) 5-AMINOSALICYLIC ACID CAPSULE FORMULATION

(71) Applicant: ALLERGAN PHARMACEUTICALS INTERNATIONAL LIMITED, Dublin (IE)

(72) Inventors: Emma Boyd, Crumlin (GB); Deborah Leigh Caldwell, Holywood (GB); Catherine Coulter, Ballymena (GB); Ryan Loughlin, Crumlin (GB); Stephen McCullagh, Belfast (GB)

(73) Assignee: Allergan Pharmaceuticals International Limited, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 16/298,634

(22) Filed: Mar. 11, 2019

(65) Prior Publication Data

US 2019/0201348 A1    Jul. 4, 2019

Related U.S. Application Data

(63) Continuation of application No. 14/474,868, filed on Sep. 2, 2014, now Pat. No. 10,265,273, which is a continuation of application No. 13/683,080, filed on Nov. 21, 2012, now abandoned.

(51) Int. Cl.
*A61K 9/48* (2006.01)
*A61K 31/606* (2006.01)
*A61K 9/28* (2006.01)

(52) U.S. Cl.
CPC .......... *A61K 9/4808* (2013.01); *A61K 9/2846* (2013.01); *A61K 9/2886* (2013.01); *A61K 9/4816* (2013.01); *A61K 31/606* (2013.01)

(58) Field of Classification Search
None
See application file for complete search history.

(56) References Cited

U.S. PATENT DOCUMENTS

| | | |
|---|---|---|
| 5,401,512 A | 3/1995 | Rhodes et al. |
| 5,541,170 A | 7/1996 | Rhodes et al. |
| 5,541,171 A | 7/1996 | Rhodes et al. |
| 5,733,575 A | 3/1998 | Mehra et al. |
| 6,022,562 A | 2/2000 | Autant et al. |
| 6,039,976 A | 3/2000 | Mehra et al. |
| 6,080,426 A | 6/2000 | Amey et al. |
| 6,245,350 B1 | 6/2001 | Amey et al. |
| 6,326,364 B1 | 12/2001 | Lin et al. |
| 6,420,473 B1 | 7/2002 | Chittamuru et al. |
| 6,569,457 B2 | 5/2003 | Ullah et al. |
| 6,649,180 B1 | 11/2003 | Matsuura et al. |
| 6,893,662 B2 | 5/2005 | Dittmar et al. |
| 7,094,425 B2 | 8/2006 | Scott et al. |
| 7,303,761 B2 | 12/2007 | Franz |
| 7,737,133 B2 | 6/2010 | Devane et al. |
| 7,833,546 B2 | 11/2010 | Petereit et al. |
| 7,964,215 B1 | 6/2011 | Ganesan et al. |
| 2002/0034541 A1 | 3/2002 | Valducci |
| 2002/0044962 A1 | 4/2002 | Cherukuri et al. |
| 2003/0096001 A1 | 5/2003 | Cherukuri et al. |
| 2003/0133983 A1 | 7/2003 | Otterbeck |
| 2005/0181053 A1 | 8/2005 | Dittmar et al. |
| 2006/0046973 A1 | 3/2006 | Kaczanowski et al. |
| 2006/0210631 A1 | 9/2006 | Patel et al. |
| 2008/0020041 A1 | 1/2008 | Ayres |
| 2009/0017110 A1 | 1/2009 | Cherukuri et al. |
| 2009/0036414 A1 | 2/2009 | Du et al. |
| 2009/0068263 A1 | 3/2009 | Antarkar et al. |
| 2010/0086588 A1 | 4/2010 | Forbes |
| 2010/0210605 A1 | 8/2010 | Kaczanowski et al. |
| 2010/0247639 A1 | 9/2010 | Ravishankar et al. |
| 2011/0223244 A1 | 9/2011 | Liversidge et al. |
| 2011/0311631 A1 | 12/2011 | Baer et al. |
| 2012/0065221 A1 | 3/2012 | Babul |
| 2012/0093939 A1 | 4/2012 | Payne et al. |
| 2012/0141592 A1 | 6/2012 | Mannello et al. |
| 2012/0282333 A1 | 11/2012 | Kakumanu et al. |
| 2013/0022681 A1 | 1/2013 | Hoeg-Moller et al. |
| 2013/0183434 A1 | 7/2013 | DeFluiter |
| 2013/0230588 A1 | 9/2013 | Speirs et al. |
| 2013/0249131 A1 | 9/2013 | Speirs et al. |
| 2013/0316000 A1 | 11/2013 | Bortey et al. |

FOREIGN PATENT DOCUMENTS

| | | |
|---|---|---|
| EP | 1 172 100 A1 | 1/2002 |
| EP | 2 659 881 A1 | 11/2013 |
| WO | 02/17887 A1 | 3/2002 |
| WO | 2010/077908 A1 | 7/2010 |
| WO | 2011/045775 A1 | 4/2011 |
| WO | 2013/134348 A1 | 9/2013 |

OTHER PUBLICATIONS

M. M. Patel, et al., "Development of a novel tablet-in-capsule formulation of mesalamine for inflammatory bowel disease", Pharmaceutical Development and Technology, pp. 1-11 (2012).

B.E. Jones, et al., "The disintegration behaviour of capsules in fed subjects: A comparison of hypromellose (carrageenan) capsules and standard gelatin capsules", International Journal of Pharmaceutics, vol. 424, pp. 40-43 (2012).

"Advantages to HPMC Capsules: A New Generation's", Drug Delivery Tech, vol. 2, No. 2, Mar./Apr. 2002.

K. Thoma, et al., "Enteric coated hard gelatin capsules", Capsugel Library, pp. 3-17.

C. Tuleu, et al., "Hypromellose capsules using carrageenan as gelling agent are bioequivalent to gelatin capsules in fed subjects", abstract.

(Continued)

*Primary Examiner* — Robert A Wax
*Assistant Examiner* — Randeep Singh
(74) *Attorney, Agent, or Firm* — Venable LLP

(57) ABSTRACT

A dosage form comprising a capsule containing one or more tablets of 5-aminosalicylic acid or a salt thereof as an active ingredient where each of the one or more tablets is enterically coated is disclosed.

18 Claims, 3 Drawing Sheets

(56) References Cited

OTHER PUBLICATIONS

H. Fadda, et al., "Comparative drug release profiles of proprietary Eudragit® S coated mesalamine tablets and plasticizer influence on drug release", abstract.
Mesalamine Delayed-Release Tablets, Official Monographs/ Mesalamine, pp. 3819-3820 (May 1, 2012).
K.H. Bauer, "Coated pharmaceutical dosage forms: Fundamentals, Manufacturing Techniques, Biopharmaceutical Aspects, Test Methods and Raw Materials", Medpharm GmbH Scientific Publishers, pp. 14-17 and 191-193 (1998).
M.Z.I. Khan, et al., "A pH-Dependent Colon-Targeted Oral Drug Delivery System Using Methacrylic Acid Copolymers. II. Manipulation of Drug Using Eudragit L100 and Eurdragit S100 Combinations," Drug Dev. and Ind. Pharm., vol. 26, No. 5, pp. 549-554 (2000).
Prescribing Information for Asacol, revised Oct. 2011.
Prescribing Information for Asacol HD, revised Oct. 2010.
International Search Report and Written Opinion of the International Searching Authority in corresponding international application PCT/IB2013/003125 filed Nov. 19, 2013.
M. Turkoglu, et al., "In vitro evaluation of pectin-HPMC compression coated 5-aminosalicylic acid tablets for colonic delivery," European Journal of Pharmaceutics and Biopharmaceutics, 53, pp. 65-73 (2002).

5-AMINOSALICYLIC ACID CAPSULE FORMULATION

This application is a continuation of U.S. application Ser. No. 14/474,868, filed on Sep. 2, 2014, which is the continuation of U.S. application Ser. No. 13/683,080, filed Nov. 21, 2012, the entire disclosure of each of which is hereby incorporated by reference herein.

BACKGROUND OF THE INVENTION

Field

This invention relates to a dosage form that is a capsule containing one or more tablets of 5-aminosalicylic acid or a salt thereof as an active ingredient and each of the one or more tablets being enterically coated. Simple encapsulation can be employed to achieve benefits in handling. It has been unexpectedly discovered that a capsule shell having a relatively low moisture content provides a dosage form that inhibits the formation of degradants within the enterically coated tablets contained within the capsule shell during the storage of the dosage form.

Related Background Art

The use of 5-aminosalicylic acid (mesalazine, mesalamine or 5-ASA) for the treatment of ulcerative colitis or Crohn's disease of the colon is well known. U.S. Pat. Nos. 5,541,170 and 5,541,171 describe dosage forms of actives, such as 5-aminosalicylic acid, that are enterically coated to facilitate delivery of the active ingredient to the colon. More specifically, a capsule dosage form containing 5-aminosalicylic acid with a gelatin capsule shell having a coating of EUDRAGIT S100 applied to the capsule shell, is exemplified. U.S. Pat. No. 6,893,662 describes dosage forms of actives, such as 5-aminosalicylic acid, having inner and outer polyacrylate coatings. None of these references discloses an enterically coated tablet of 5-aminosalicylic acid in a capsule.

It is known that 5-aminosalicylic acid dosage forms formulated with a reducing sugar, such as lactose, are subject to degradation, particularly when prepared using an aqueous wet granulation technique or subjected to high humidity. This degradation will produce a breakdown product (5-[2-formyl-5-(hydroxymethyl-1H-pyrrol-1-yl]-2-hydroxybenzoic acid (herein referred to as degradant B or deg B) that can limit shelf life and reduce the performance of the product. It has been surprisingly found that encapsulation of enterically coated tablets can enhance stability. U.S. Patent Application Publication No. 2010/0210605 teaches that such degradation may be reduced by providing a dosage form in a kit with a predetermined amount of desiccant. While the use of low moisture hydroxypropylmethyl cellulose (HPMC) capsules was known for use with capsule fills of water-sensitive actives (see HPMC Capsules: New Generation Drug Delivery Technology, Vol. 2, No. 2, March/April 2002), there was little expectation that the moisture content of a capsule would have a discernible effect on the stability of an enterically coated tablet of 5-aminosalicylic acid contained therein.

SUMMARY OF THE INVENTION

Figure 1:
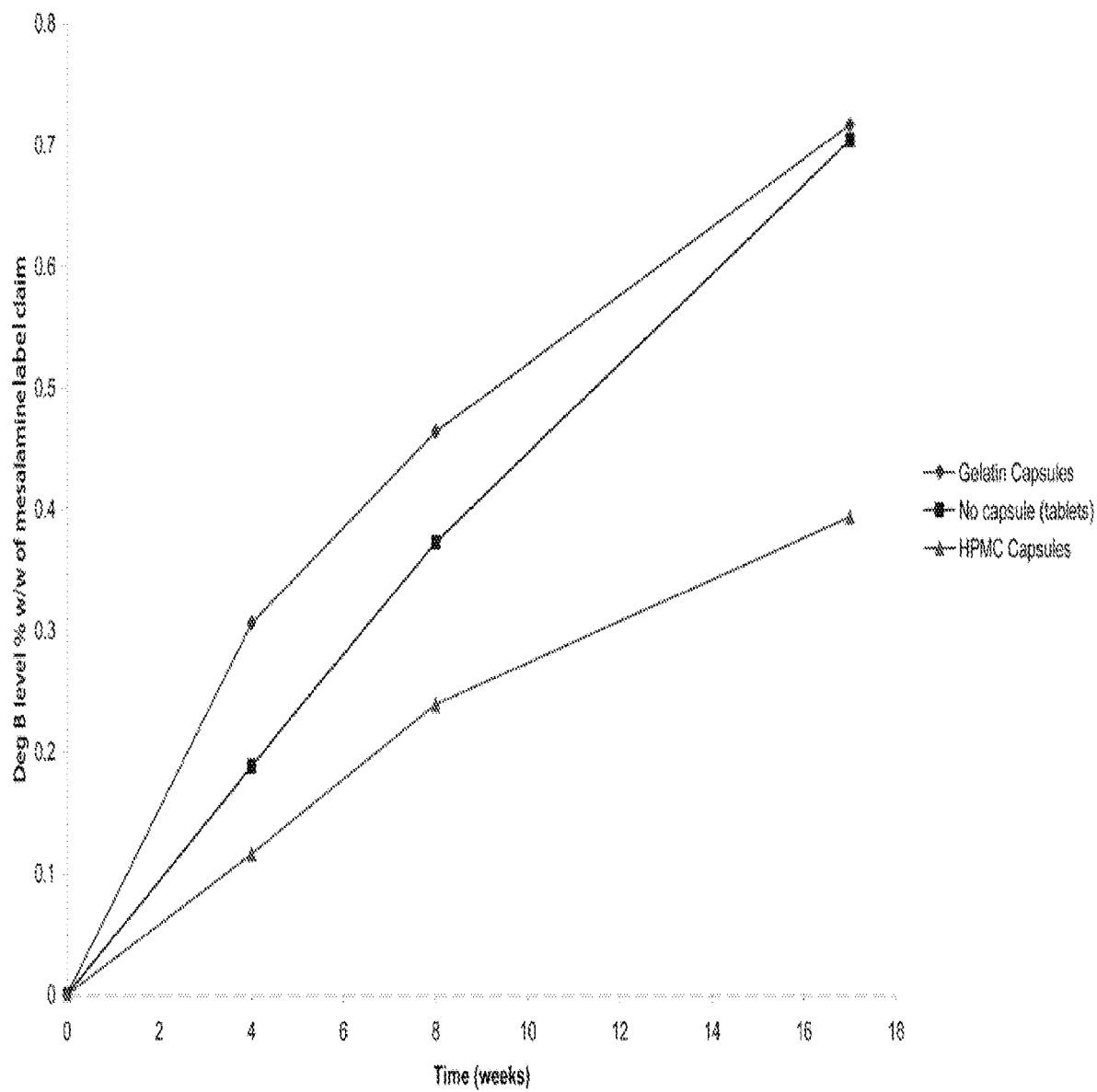
FIG. 1 is a plot of degradant B level over a 17 week storage period at 40° C./75% relative humidity, i.e., ICH accelerated conditions, for dosage forms utilizing an HPMC capsule shell, dosage forms utilizing a gelatin capsule shell, and for enterically coated tablets which are not contained in a capsule shell.

The inventive dosage form comprises (a) a capsule shell; and (b) at least one tablet within the capsule shell, the at least one tablet containing 5-aminosalicylic acid or a salt thereof as an active ingredient and having an enteric coat.

The inventive dosage form may also comprise (a) a capsule shell having less than about 10% by weight moisture content in the capsule shell at a relative humidity of 60% and a temperature of 25° C.; and (b) at least one tablet within the capsule shell, the at least one tablet containing 5-aminosalicylic acid or a salt thereof as an active ingredient and having an enteric coat.

According to the invention, the one or more tablets contain a total of about 50 mg to about 1,800 mg of 5-aminosalicylic acid. In a certain embodiment of the invention, the capsule shell comprises HPMC. In certain embodiments, the enteric coat comprises a single enteric coating or a plurality of enteric coatings. In preferred embodiments, the enteric coat comprises an inner layer of a first polyacrylic acid copolymer enteric coating and an outer layer of a second polyacrylic acid copolymer enteric coating that is different than the inner layer. Alternatively, in preferred embodiments, the inner layer of enteric coating is poly (methacrylic acid, methyl methacrylate) 1:2 and the outer layer of enteric coating is poly(methacrylic acid, methyl methacrylate) 1:1. The outer layer is applied on to the inner layer.

In certain embodiments, the enteric coat contains iron oxide, the enteric coat provides delivery of the active ingredient to the colon of a human, or the enteric coat comprises a material selected from film coatings, cellulose derivatives, cellulose ethers, methyl cellulose, ethylcellulose, carboxymethylcellulose, carboxymethylethylcellulose, hydroxyethyl cellulose, hydroxypropyl cellulose, hydroxypropyl methylcellulose, low viscosity hydroxypropyl cellulose, low viscosity hydroxypropyl methylcellulose, wax or wax like substance, such as carnauba wax, fatty alcohols, hydrogenated vegetable oils, zein, shellac, sucrose, Arabic gum, polyethylene glycol, polyvinylpyrolidone, gelatin, sodium alginate, dextrin, psyllium husk powder, polymethacrylates, anionic polymethacrylates, poly(methacrylic acid, methyl methacrylate) 1:2 (Eudragit®S), poly(methacrylic acid, methyl methacrylate) 1:1 (Eudragit®L), cellulose acetate phthalate, cellulose acetate trimelliate, hydroxypropyl methylcellulose phthalate (HPMCP), cellulose propionate phthalate, cellulose acetate maleate, polyvinyl alcohol phthalate, hydroxypropyl methylcellulose acetate succinate (HPMCAS), hydroxypropyl methylcellulose hexahydrophthalate, polyvinyl acetate phthalate, poly(methacrylic acid, ethyl acrylate) 1:1, and combinations thereof.

The invention is also directed to a kit comprising a dosage form of the present invention and a predetermined amount of desiccant.

The invention is further directed to a method of treating an inflammatory condition of the gastrointestinal tract comprising administering a dosage form of the present invention to a patient in need of treatment.

The invention is still further directed to a method of improving the handling properties of a 5-aminosalicylic acid dosage form comprising the step of: providing at least one tablet containing 5-aminosalicylic acid or a salt thereof as an active ingredient and having an enteric coat; and encapsulating the at least one tablet in a capsule shell.

The invention is still further directed to a method of improving the stability of a 5-aminosalicylic acid dosage form comprising the steps of: providing at least one tablet containing 5-aminosalicylic acid or a salt thereof as an active ingredient and having an enteric coat; and encapsulating the at least one tablet in a capsule shell, wherein the capsule shell has less than about 10% by weight moisture content at a relative humidity of 60% and a temperature of 25° C.

Another embodiment of the invention is directed to a method of modifying the dissolution profile of a dosage form upon storage comprising the step of: providing the dosage form in a kit comprising the dosage form and a predetermined amount of desiccant, wherein the dosage form has (a) a capsule shell having less than about 10% by weight moisture content in the capsule shell at a relative humidity of 60% and a temperature of 25° C. and (b) at least one tablet within the capsule shell, the at least one tablet containing 5-aminosalicylic acid or a salt thereof as an active ingredient and having an enteric coat. In a preferred embodiment, the dissolution profile of the dosage form upon storage is substantially similar to the dissolution profile of the dosage form upon manufacture.

DETAILED DESCRIPTION

A first embodiment of the present invention is directed to a dosage form comprising (a) a capsule shell; and (b) at least one tablet within the capsule shell, the at least one tablet containing 5-aminosalicylic acid or a salt thereof as an active ingredient and having an enteric coat. The dosage form of the present invention has improved handling properties. As used herein, "improved handling properties" refers to a decreased need to employ soft handling techniques when handling the dosage forms of the present invention. It is known that handling enterically coated 5-aminosalicylic acid tablets using conventional means may cause differences in product performance due to damage done to the coating, i.e., coating fracture; dosage forms of the present invention can be more readily handled, i.e., without the need for soft handling techniques.

The capsule shell may comprise any material conventional in the art for capsules. In certain preferred embodiments, the capsule shell comprises, as a primary component, gelatin, HPMC, polyvinyl alcohol (PVA), pullulan, carageenan or a combination thereof. The capsule shell may include additives such as carageenan, pigments such as titanium dioxide and iron oxides, potassium chloride or combinations thereof. When present, one of ordinary skill in the art can readily determine a suitable amount of such additives. It is believed that capsule shells such as those disclosed in U.S. Pat. No. 6,649,180 may be useful in the present invention.

The capsule shell may be purchased from commercially available sources or made according to known methods. There is no limitation on the size of the capsule shell, and it may be selected from commercially available sizes such as 0, 00, 0el, AAel, 000 and AAA. Preferably the capsule shell is size 0.

The dosage form of the present invention also comprises one or more tablets within the capsule shell, the one or more tablets containing 5-aminosalicylic acid or a salt thereof as an active ingredient and having an enteric coat. As used herein, "or a salt thereof" refers to any salt of 5-aminosalicylic acid formed with a suitable counterion such as potassium, calcium, sodium or zinc. In certain embodiments of the invention, the tablet comprises mesalamine potassium or mesalimine sodium. The 5-aminosalicylic acid or salt thereof may be purchased from known sources or made according to known methods.

Preferably, the capsule shell contains one or four tablets, but may contain two, three, five or more tablets. Importantly, each of the tablets contains 5-aminosalicylic acid or a salt thereof and has an enteric coat. In a preferred embodiment, the tablet(s) may be mesalamine delayed-release tablets. The tablets may be placed inside the capsule in any conventional manner without the need for cushioning materials or additional excipients.

Tablet(s) suitable for use in the present invention are not limited by size or shape, but are of such size and shape as to be readily ingested and swallowed. Typically, the tablet(s) are spherical, oblong, or elliptical. In a preferred embodiment of the invention, the tablets are greater than about 5 mm in diameter and no more than about 12 mm in diameter; in a preferred embodiment of the invention, the tablets are greater than about 5 mm in length and no more than about 30 mm in length. Tablets suitable for use in the present invention are distinguished from "granulated" formulations and "granulations" of 5-aminosalicylic acid with regard to at least size; further "tablets" as used herein have necessarily been compressed or subjected to compression techniques. Tablet(s) suitable for use in the present invention are likewise not limited by method of manufacture. They may be made by any conventional compression or granulation (wet or dry) technique. What is more, the tablet(s) may be purchased from commercially available sources or made according to known methods.

Tablet(s) suitable for use in the present invention may have any composition as long as they contain 5-aminosalicylic acid or a salt thereof. Tablet(s) may comprise any ingredients useful in pharmaceutical manufacture and suitable for 5-aminosalicylic acid formulations. Suitable additional ingredients or excipients include, without limitation, sugars, such as lactose and glucose; starches, such as cornstarch, potato starch, and sodium starch glycolate; cellulose and its derivatives, such as sodium carboxymethyl cellulose, ethyl cellulose, cellulose acetate, hypromellose, hydroxypropyl methyl cellulose, methyl cellulose, microcrystalline cellulose; powdered tragacanth; malt; gelatin; talc; solid lubricants, such as stearic acid, magnesium stearate, or calcium sulfate; vegetable oils, such as peanut oil, cottonseed oil, sesame oil, olive oil, corn oil, and oil of theobroma; polyols such as propylene glycol, glycerin, sorbitol, mannitol, and polyethylene glycol; alginic acid; emulsifiers/surfactants, such as polysorbate detergents (Tweens®); wetting agents such as sodium lauryl sulfate; coloring agents; flavoring agents; excipients; tableting agents; stabilizers; antioxidants; preservatives; fillers; binders; lubricants; disintegrants; pyrogen-free water; isotonic saline; phosphate buffer solutions; and combinations thereof. Excipients suitable for use in the present invention are generally described in Remington's Pharmaceutical Sciences, Mack Publishing Co. (19th edit. 1995); Modern Pharmaceutics, Vol. 7, Chapters 9 & 10, Banker & Rhodes (1979); Lieberman, et al, Pharmaceutical Dosage Forms: Tablets (1981); and Ansel, Introduction to Pharmaceutical Dosage Forms, 2d (1976).

An exact tablet formulation can be readily selected according to criteria well known to those skilled in the art.

The one or more tablets of the present invention preferably contain a total of about 50 mg to about 1,800 mg of 5-aminosalicylic acid. When the dosage form of the present invention contains more than one tablet, then the tablets may each contain the same or a different amount of 5-aminosalicylic acid. In a preferred embodiment of the present invention, the dosage form contains one tablet having 400 mg, 600 mg or 800 mg 5-aminosalicylic acid. In another preferred embodiment, the dosage form contains four tablets, each having 50 mg, 100 mg, or 150 mg 5-aminosalicylic acid.

According to the invention, the tablet(s) has an enteric coat. As used herein, "coat" or "coating" refers to completely encasing or covering the entire surface of a tablet. In certain preferred embodiments, the coat or coating is a film coating, sugar coating or a specialized coating such as compression coating, electrostatic coating, dip coating or vacuum film coating. In certain preferred embodiments, the tablet(s) has an enteric coat according to U.S. Pat. Nos. 5,541,170 or 5,541,171 or 6,893,662, the disclosure of each of which is incorporated by reference herein. In a preferred embodiment of the present invention, the capsule shell is not itself enterically coated, but rather only the tablet(s) inside is enterically coated.

Generally, the enteric coat may comprise any material capable of delivering the 5-aminosalicylic acid or a salt thereof to the colon of a human, i.e., capable of preventing the release of 5-aminosalicylic acid prior to reaching the colon of a human or capable of preventing release in the upper gastrointestinal tract. More preferably, delivery of the 5-aminosalicylic acid is to the right side of the colon. In another preferred embodiment of the invention, the drug-release profile of the dosage form is pH dependent.

In preferred embodiments, the enteric coat may comprise, without limitation, poly(methacrylic acid, methyl methacrylate) 1:2 (Eudragit®S), poly(methacrylic acid, methyl methacrylate) 1:1 (Eudragit®L), and mixtures thereof. In other preferred embodiments, the enteric coat may comprise, without limitation, film coatings, cellulose derivatives, cellulose ethers, methyl cellulose, ethylcellulose, carboxymethylcellulose, carboxymethylethylcellulose, hydroxyethyl cellulose, hydroxypropyl cellulose, hydroxypropyl methylcellulose, low viscosity hydroxypropyl cellulose, low viscosity hydroxypropyl methylcellulose, wax or wax like substance, such as carnauba wax, fatty alcohols, hydrogenated vegetable oils, zein, shellac, sucrose, Arabic gum, polyethylene glycol, polyvinylpyrolidone, gelatin, sodium alginate, dextrin, psyllium husk powder, polymethacrylates, anionic polymethacrylates, poly(methacrylic acid, methyl methacrylate) 1:2 (Eudragit®S), poly(methacrylic acid, methyl methacrylate) 1:1 (Eudragit®L), cellulose acetate phthalate, cellulose acetate trimelliate, hydroxypropyl methylcellulose phthalate (HPMCP), cellulose propionate phthalate, cellulose acetate maleate, polyvinyl alcohol phthalate, hydroxypropyl methylcellulose acetate succinate (HPMCAS), hydroxypropyl methylcellulose hexahydrophthalate, polyvinyl acetate phthalate, poly(methacrylic acid, ethyl acrylate) 1:1, and mixtures thereof. One of ordinary skill in the art will readily appreciate that the foregoing list comprises a number of enteric as well as non-enteric materials; the present invention requires the presence of an enteric coat. Therefore, at least one enteric material must be present either in the presence or absence of other non-enteric materials. In addition, other enteric polymer materials which have the same pH release characteristics in aqueous media as, e.g., Eudragit®S, may also be suitable for use as the enteric coat of the present invention. In other preferred embodiments, the enteric coating is soluble at a pH of 6.4 or greater. In other preferred embodiments, the enteric coating begins to dissolve in an aqueous media, e.g., an aqueous buffer, at a pH of about 7.0. In still other preferred embodiments, the enteric coating begins to dissolve in an aqueous media, e.g., an aqueous buffer, at a pH of about 6.0.

Preferably the enteric coat of the present invention also comprises a plasticizer. Appropriate plasticizers include polyethylene glycols, propylene glycols, 1,2-propylene glycol, dibutyl phthalate, dibutyl sebacate, diethyl phthalate, tributyl citrate, triethyl citrate, tributyrin, butyl phthalyl butyl glycolate, triacetin, castor oil, citric acid esters, and combinations thereof. Plasticizer(s) are present in an amount to facilitate the coating process and to obtain an even coating film with enhanced physical stability. One of ordinary skill in the art would readily determine a suitable amount of plasticizer(s) for inclusion.

In addition, to facilitate the coating process, the coating material may also comprise inert solid particulates. Preferred inert solid particulates include talc, iron oxide and titanium dioxide. When present, one of ordinary skill in the art can readily determine a suitable amount for inclusion.

Generally, the enteric coat suitable for use in the present invention comprises a single enteric coating or a plurality of enteric coatings. When a plurality of enteric coatings is employed, then each of the plurality of enteric coatings may be the same or different in thickness and/or composition. In one embodiment of the invention, the total thickness of the coating ranges preferably from about 50 µm to about 250 µm, more preferably from about 75 µm to about 175 µm, and most preferably from about 100 µm to about 150 µm; in a more preferred embodiment, at least two coatings comprise the noted total thickness. In another preferred embodiment, the total thickness of a single enteric coating ranges preferably from about 40 µm to about 110 µm, more preferably from about 55 µm to about 95 µm, and most preferably from about 70 µm to about 80 µm. In yet another preferred embodiment, the total thickness of a combination of at least two enteric coatings ranges preferably from about 60 µm to about 125 µm, more preferably from about 75 µm to about 110 µm, and most preferably from about 90 µm to about 95 µm; in a more preferred embodiment, the thickness of an inner coating is approximately double that of an outer coating.

A suitable amount of coating can also be specified by referring to weight gain per surface area for a given tablet. In one embodiment of the invention, the weight gain per surface area ranges preferably from about 1 mg/cm$^2$ to about 22 mg/cm$^2$, more preferably from about 6 mg/cm$^2$ to about 17 mg/cm$^2$, and most preferably from about 11 mg/cm$^2$ to about 12 mg/cm$^2$; in a more preferred embodiment, at least two coatings comprise the noted total weight gain. In another preferred embodiment, the weight gain per surface area of a single enteric coating ranges preferably from about 3 mg/cm$^2$ to about 16 mg/cm$^2$, more preferably from about 6 mg/cm$^2$ to about 13 mg/cm$^2$, and most preferably from about 9 mg/cm$^2$ to about 10 mg/cm$^2$. In yet another preferred embodiment, the weight gain per surface area of a combination of at least two enteric coatings ranges preferably from about 6 mg/cm$^2$ to about 19 mg/cm$^2$, more preferably from about 9 mg/cm$^2$ to about 16 mg/cm$^2$, and most preferably from about 12 mg/cm$^2$ to about 13 mg/cm$^2$; in a more preferred embodiment, the weight gain attributable to an inner coating is approximately double that of an outer coating.

The enteric coat of the present invention may be applied to the tablet(s) of the present invention in any manner known in the art, typically through the application of enteric polymers onto the tablet(s) as solutions in organic solvents or as solutions/suspensions in aqueous media, followed by drying and curing. Solvents commonly employed as vehicles are water, methylene chloride, ethanol, methanol, isopropyl alcohol, acetone, ethyl acetate and combinations thereof. The choice of the solvent is based primarily on the solubility of the polymer, ease of evaporation, and viscosity of the solution. Some polymers are also available as aqueous systems. These include Eudragit®L30D (methacrylic acid-ethyl acrylate ester copolymer marketed by Rohm-Haas GmBH, West Germany); Aquateric® (cellulose acetate phthalate-containing product marketed by FMC Corporation, Philadelphia, Pa.); and Coateric® (a polyvinyl acetate phthalate based product marketed by Colorcon, Inc., West Point, Pa.). Coating can be achieved by methods known to one skilled in the art such as by using fluidized bed equipment, perforated pans, a regular pharmaceutical pan, compression coating, continuous or short spray methods, or by drenching. Likewise drying or curing of the enteric coat (either single or multiple coats) may be accomplished by any known means. When more than one enteric coat is present, an outer coating layer is applied after an inner coating layer, but may be applied before, during or after the inner coating layer is dried and/or cured.

In a certain preferred embodiment of the invention, a single enteric coating or at least one of a plurality of enteric coatings is a polyacrylic acid copolymer. In a certain preferred embodiment, the enteric coat of the one or more tablets comprises a single enteric coating comprised of a polyacrylic acid copolymer. In a certain preferred embodiment, the enteric coat comprises an inner layer of a first polyacrylic acid copolymer enteric coating and an outer layer of a polyacrylic acid copolymer enteric coating that is different than the inner layer, and more preferably the inner layer of enteric coating is poly(methacrylic acid, methyl methacrylate) 1:2 and the outer layer of enteric coating is poly(methacrylic acid, methyl methacrylate) 1:1. In certain embodiments, the single enteric coating will be Eudragit®S. In other embodiments, the inner enteric coating will comprise Eudragit®S, and the outer enteric coating will comprise Eudragit®L.

When more than one tablet is present in the capsule, then the tablets may have the same or different composition, size and/or shape and the same or different enteric coat.

A second embodiment of the present invention is directed to a dosage form comprising (a) a capsule shell having less than about 10% by weight moisture content in the capsule shell at a relative humidity of 60% and a temperature of 25° C.; and (b) at least one tablet within the capsule shell, the at least one tablet containing 5-aminosalicylic acid or a salt thereof as an active ingredient and having an enteric coat. The dosage forms of this embodiment have improved stability, i.e., decreased presence of 5-[2-formyl-5-(hydroxymethyl-1H-pyrrol-1-yl]-2-hydroxybenzoic acid (degradant B) upon storage, etc., as compared to enterically coated tablets and, in a preferred embodiment, as compared to similar dosage forms employing capsule shells with too high a moisture content. Degradant B is a typical degradant upon storage of 5-aminosalicylic acid formulations produced using a reducing sugar such as lactose. In one embodiment, "stable" or "stability" refers to a dosage form which accumulates no more than about 0.15% w/w degradant B upon storage at a relative humidity of 60% and a temperature of 25° C., when measured according to a recognized stability testing method under International Conference on Harmonization (ICH) storage conditions. As used herein, "improved stability" or "improving stability" refers to a dosage form of the present invention which achieves stability as defined above, i.e., which accumulates less degradant B upon storage as compared to a control such as enterically coated tablets and dosage forms employing capsule shells with too high a moisture content. Preferably the dosage forms of the present invention are stable for a period of at least 6 months, more preferably at least 12 months, and most preferably at least 18 months when stored without desiccant; preferably the dosage forms of the present invention are stable for a period of at least 12 months, more preferably at least 24 months, and most preferably at least 36 months when stored with a suitable amount of desiccant.

The capsule shell suitable for use in this embodiment of the invention is a capsule shell having less than about 10% by weight moisture content at a relative humidity of 60% and a temperature of 25° C. More preferably, the weight moisture content of the capsule shell is less than about 7.5% at a relative humidity of 60% and a temperature of 25° C. Preferred weight moisture content of the capsule will depend upon the storage conditions. For example, further preferred embodiments of the invention are those in which the weight moisture content of the capsule shell is less than about 6% at a relative humidity of 50% and a temperature of 25° C. or in which the weight moisture content of the capsule shell is less than about 11.5% at a relative humidity of 75% and a temperature of 40° C. Moisture content is expressed as the equilibrium moisture content and was determined using a conventional Dynamic Vapor Sorption (DVS) technique.

The capsule shell may comprise any material which allows for attainment of the noted weight moisture content. In certain preferred embodiments, the capsule shell comprises HPMC, polyvinyl alcohol (PVA) or a combination thereof. The capsule shell may include additives such as carageenan, pigments such as titanium dioxide and iron oxides, potassium chloride or combinations thereof. When present, one of ordinary skill in the art can readily determine a suitable amount of such additives. It is believed that capsule shells such as those disclosed in U.S. Pat. No. 6,649,180 may be useful in the present invention.

The capsule shell may be purchased from commercially available sources or made according to known methods. There is no limitation on the size of the capsule shell, and it may be selected from commercially available sizes such as 0, 00, 0el, AAel, 000 and AAA. Preferably the capsule shell is size 0.

The dosage form of the present invention also comprises one or more tablets within the capsule shell, the one or more tablets containing 5-aminosalicylic acid or a salt thereof as an active ingredient and having an enteric coat. As used herein, "or a salt thereof" refers to any salt of 5-aminosalicylic acid formed with a suitable counterion such as potassium, calcium, sodium or zinc. In certain embodiments of the invention, the tablet comprises mesalamine potassium or mesalimine sodium. The 5-aminosalicylic acid or salt thereof may be purchased from known sources or made according to known methods.

Preferably, the capsule shell contains one or four tablets, but may contain two, three, five or more tablets. Importantly, each of the tablets contains 5-aminosalicylic acid or a salt thereof and has an enteric coat. In a preferred embodiment, the tablet(s) may be mesalamine delayed-release tablets. The tablets may be placed inside the capsule in any conventional manner without the need for cushioning materials or additional excipients.

Tablet(s) suitable for use in the present invention are not limited by size or shape, but are of such size and shape as to be readily ingested and swallowed. Typically, the tablet(s) are spherical, oblong, or elliptical. In a preferred embodiment of the invention, the tablets are greater than about 5 mm in diameter and no more than about 12 mm in diameter; in a preferred embodiment of the invention, the tablets are greater than about 5 mm in length and no more than about 30 mm in length. Tablets suitable for use in the present invention are distinguished from "granulated" formulations and "granulations" of 5-aminosalicylic acid with regard to at least size; further "tablets" as used herein have necessarily been compressed or subjected to compression techniques.

Tablet(s) suitable for use in the present invention are likewise not limited by method of manufacture. They may be made by any conventional compression or granulation (wet or dry) technique. What is more, the tablet(s) may be purchased from commercially available sources or made according to known methods. The invention is particularly suited to 5-aminosalicylic acid tablets, which are formulated with a reducing sugar, such as lactose, and which are subject to degradation, particularly when prepared using an aqueous wet granulation technique or subjected to high humidity.

Tablet(s) suitable for use in the present invention may have any composition as long as they contain 5-aminosalicylic acid or a salt thereof. Preferably tablet(s) suitable for use in the present invention also contain a reducing sugar such as lactose. Tablet(s) may comprise any ingredients useful in pharmaceutical manufacture and suitable for 5-aminosalicylic acid formulations. Suitable additional ingredients or excipients include, without limitation, sugars, such as lactose and glucose; starches, such as cornstarch, potato starch, and sodium starch glycolate; cellulose and its derivatives, such as sodium carboxymethyl cellulose, ethyl cellulose, cellulose acetate, hypromellose, hydroxypropyl methyl cellulose, methyl cellulose, microcrystalline cellulose; powdered tragacanth; malt; gelatin; talc; solid lubricants, such as stearic acid, magnesium stearate, or calcium sulfate; vegetable oils, such as peanut oil, cottonseed oil, sesame oil, olive oil, corn oil, and oil of theobroma; polyols such as propylene glycol, glycerin, sorbitol, mannitol, and polyethylene glycol; alginic acid; emulsifiers/surfactants such as polysorbate detergents (Tweens®); wetting agents such as sodium lauryl sulfate; coloring agents; flavoring agents; excipients; tableting agents; stabilizers; antioxidants; preservatives; fillers; binders; lubricants; disintegrants; pyrogen-free water; isotonic saline; phosphate buffer solutions; and combinations thereof. Excipients suitable for use in the present invention are generally described in Remington's Pharmaceutical Sciences, Mack Publishing Co. (19th edit. 1995); Modern Pharmaceutics, Vol. 7, Chapters 9 & 10, Banker & Rhodes (1979); Lieberman, et al, Pharmaceutical Dosage Forms: Tablets (1981); and Ansel, Introduction to Pharmaceutical Dosage Forms, 2d (1976). An exact tablet formulation can be readily selected according to criteria well known to those skilled in the art.

The one or more tablets of the present invention preferably contain a total of about 50 mg to about 1,800 mg of 5-aminosalicylic acid. When the dosage form of the present invention contains more than one tablet, then the tablets may each contain the same or a different amount of 5-aminosalicylic acid. In a preferred embodiment of the present invention, the dosage form contains one tablet having 400 mg, 600 mg or 800 mg 5-aminosalicylic acid. In another preferred embodiment, the dosage form contains four tablets, each having 50 mg, 100 mg, or 150 mg 5-aminosalicylic acid.

According to the invention, the tablet(s) has an enteric coat. As used herein, "coat" or "coating" refers to completely encasing or covering the entire surface of a tablet. In certain preferred embodiments, the coat or coating is a film coating, sugar coating or a specialized coating such as compression coating, electrostatic coating, dip coating or vacuum film coating. In certain preferred embodiments, the tablet(s) has an enteric coat according to U.S. Pat. Nos. 5,541,170 or 5,541,171 or 6,893,662, the disclosure of each of which is incorporated by reference herein. In a preferred embodiment of the present invention, the capsule shell is not itself enterically coated, but rather only the tablet(s) inside is enterically coated.

Generally, the enteric coat may comprise any material capable of delivering the 5-aminosalicylic acid to the colon of a human, i.e., capable of preventing the release of 5-aminosalicylic acid prior to reaching the colon of a human or capable of preventing release in the upper gastrointestinal tract. More preferably, delivery of the 5-aminosalicylic acid is to the right side of the colon. In another preferred embodiment of the invention, the drug-release profile of the dosage form is pH dependent.

In preferred embodiments, the enteric coat may comprise, without limitation, poly(methacrylic acid, methyl methacrylate) 1:2 (Eudragit®S), poly(methacrylic acid, methyl methacrylate) 1:1 (Eudragit®L), and mixtures thereof. In other preferred embodiments, the enteric coat may comprise, without limitation, film coatings, cellulose derivatives, cellulose ethers, methyl cellulose, ethylcellulose, carboxymethylcellulose, carboxymethylethylcellulose, hydroxyethyl cellulose, hydroxypropyl cellulose, hydroxypropyl methylcellulose, low viscosity hydroxypropyl cellulose, low viscosity hydroxypropyl methylcellulose, wax or wax like substance, such as carnauba wax, fatty alcohols, hydrogenated vegetable oils, zein, shellac, sucrose, Arabic gum, polyethylene glycol, polyvinylpyrolidone, gelatin, sodium alginate, dextrin, psyllium husk powder, polymethacrylates, anionic polymethacrylates, poly(methacrylic acid, methyl methacrylate) 1:2 (Eudragit®S), poly(methacrylic acid, methyl methacrylate) 1:1 (Eudragit®L), cellulose acetate phthalate, cellulose acetate trimelliate, hydroxypropyl methylcellulose phthalate (HPMCP), cellulose propionate phthalate, cellulose acetate maleate, polyvinyl alcohol phthalate, hydroxypropyl methylcellulose acetate succinate (HPM-CAS), hydroxypropyl methylcellulose hexahydrophthalate, polyvinyl acetate phthalate, poly(methacrylic acid, ethyl acrylate) 1:1, and mixtures thereof. One of ordinary skill in the art will readily appreciate that the foregoing list comprises a number of enteric as well as non-enteric materials; the present invention requires the presence of an enteric coat. Therefore, at least one enteric material must be present either in the presence or absence of other non-enteric materials. In addition, other enteric polymer materials which have the same pH release characteristics in aqueous media as, e.g., Eudragit®S, may also be suitable for use as the enteric coat of the present invention. In other preferred embodiments, the enteric coating is soluble at a pH of 6.4 or greater. In other preferred embodiments, the enteric coating begins to dissolve in an aqueous media, e.g., an aqueous buffer, at a pH of about 7.0. In still other preferred embodiments, the enteric coating begins to dissolve in an aqueous media, e.g., an aqueous buffer, at a pH of about 6.0.

Preferably the enteric coat of the present invention also comprises a plasticizer. Appropriate plasticizers include polyethylene glycols, propylene glycols, 1,2-propylene glycol, dibutyl phthalate, dibutyl sebacate, diethyl phthalate, tributyl citrate, triethyl citrate, tributyrin, butyl phthalyl butyl glycolate, triacetin, castor oil, citric acid esters, and combinations thereof. Plasticizer(s) are present in an amount to facilitate the coating process and to obtain an even coating film with enhanced physical stability. One of ordinary skill in the art would readily determine a suitable amount of plasticizer(s) for inclusion.

In addition, to facilitate the coating process, the coating material may also comprise inert solid particulates. Preferred inert solid particulates include talc, iron oxide and titanium dioxide. When present, one of ordinary skill in the art can readily determine a suitable amount for inclusion.

Generally, the enteric coat suitable for use in the present invention comprises a single enteric coating or a plurality of enteric coatings. When a plurality of enteric coatings is employed, then each of the plurality of enteric coatings may be the same or different in thickness and/or composition. In one embodiment of the invention, the total thickness of the coating ranges preferably from about 50 µm to about 250 µm, more preferably from about 75 µm to about 175 µm, and most preferably from about 100 µm to about 150 µm; in a more preferred embodiment, at least two coatings comprise the noted total thickness. In another preferred embodiment, the total thickness of a single enteric coating ranges preferably from about 40 µm to about 110 µm, more preferably from about 55 µm to about 95 µm, and most preferably from about 70 µm to about 80 µm. In yet another preferred embodiment, the total thickness of a combination of at least two enteric coatings ranges preferably from about 60 µm to about 125 µm, more preferably from about 75 µm to about 110 µm, and most preferably from about 90 µm to about 95 µm; in a more preferred embodiment, the thickness of an inner coating is approximately double that of an outer coating.

A suitable amount of coating can also be specified by referring to weight gain per surface area for a given tablet. In one embodiment of the invention, the weight gain per surface area ranges preferably from about 1 mg/cm$^2$ to about 22 mg/cm$^2$, more preferably from about 6 mg/cm$^2$ to about 17 mg/cm$^2$, and most preferably from about 11 mg/cm$^2$ to about 12 mg/cm$^2$; in a more preferred embodiment, at least two coatings comprise the noted total weight gain. In another preferred embodiment, the weight gain per surface area of a single enteric coating ranges preferably from about 3 mg/cm$^2$ to about 16 mg/cm$^2$, more preferably from about 6 mg/cm$^2$ to about 13 mg/cm$^2$, and most preferably from about 9 mg/cm$^2$ to about 10 mg/cm$^2$. In yet another preferred embodiment, the weight gain per surface area of a combination of at least two enteric coatings ranges preferably from about 6 mg/cm$^2$ to about 19 mg/cm$^2$, more preferably from about 9 mg/cm$^2$ to about 16 mg/cm$^2$, and most preferably from about 12 mg/cm$^2$ to about 13 mg/cm$^2$; in a more preferred embodiment, the weight gain attributable to an inner coating is approximately double that of an outer coating.

The enteric coat of the present invention may be applied to the tablet(s) of the present invention in any manner known in the art, typically through the application of enteric polymers onto the tablet(s) as solutions in organic solvents or as solutions/suspensions in aqueous media, followed by drying and curing. Solvents commonly employed as vehicles are water, methylene chloride, ethanol, methanol, isopropyl alcohol, acetone, ethyl acetate and combinations thereof. The choice of the solvent is based primarily on the solubility of the polymer, ease of evaporation, and viscosity of the solution. Some polymers are also available as aqueous systems. These include Eudragit®L3OD (methacrylic acid-ethyl acrylate ester copolymer marketed by Rohm-Haas GmBH, West Germany); Aquateric® (cellulose acetate phthalate-containing product marketed by FMC Corporation, Philadelphia, Pa.); and Coateric® (a polyvinyl acetate phthalate based product marketed by Colorcon, Inc., West Point, Pa.). Coating can be achieved by methods known to one skilled in the art such as by using fluidized bed equipment, perforated pans, a regular pharmaceutical pan, compression coating, continuous or short spray methods, or by drenching. Likewise drying or curing of the enteric coat (either single or multiple coats) may be accomplished by any known means. When more than one enteric coat is present, an outer coating layer is applied after an inner coating layer, but may be applied before, during or after the inner coating layer is dried and/or cured.

In a certain preferred embodiment of the invention, a single enteric coating or at least one of a plurality of enteric coatings is a polyacrylic acid copolymer. In a certain preferred embodiment, the enteric coat of the one or more tablets comprises a single enteric coating comprised of a polyacrylic acid copolymer. In a certain preferred embodiment, the enteric coat comprises an inner layer of a first polyacrylic acid copolymer enteric coating and an outer layer of a polyacrylic acid copolymer enteric coating that is different than the inner layer, and more preferably the inner layer of enteric coating is poly(methacrylic acid, methyl methacrylate) 1:2 and the outer layer of enteric coating is poly(methacrylic acid, methyl methacrylate) 1:1. In certain embodiments, the single enteric coating will be Eudragit®S. In other embodiments, the inner enteric coating will comprise Eudragit®S, and the outer enteric coating will comprise Eudragit®L.

When more than one tablet is present in the capsule, then the tablets may have the same or different composition, size and/or shape and the same or different enteric coat.

The dosage forms of the first and second embodiments of the present invention are preferably packaged as part of a kit which comprises at least one of the present dosage forms and a predetermined amount of desiccant. Therefore, a third embodiment of the invention is directed to such a kit.

As used herein, a "desiccant" is a material that will absorb moisture by physical and/or chemical means. Activated desiccants are desiccants that have been treated by heating and ventilating, or by other means, to develop an internal surface on which moisture and certain vapors or gases may collect. Common desiccants include, but are not limited to, silica gel, indicating silica gel, molecular sieves, clay or montmorillonite, activated carbon, alumina, and combinations thereof. Suitable desiccants are commercially available, either in bulk or predetermined amounts, or may be made according to known methods.

Desiccant quantities may be adjusted depending on the need of the application. For example, a bulk product may be stored in a drum with a suitable amount of a desiccant, or it may first be divided into smaller batches and stored appropriately with a smaller quantity of a desiccant. The moisture initially in a package from the drug substance, excipients, and fillers, as well as moisture permeation into the package over its shelf life, will determine the amount of desiccant required in a given package. The quantity of desiccant in an ideal case should be at least sufficient to absorb this moisture and maintain a desiccated environment within the package for the product's shelf life.

Desiccant Quantity Calculation

> Total moisture to be absorbed by desiccant (g)=product moisture (g)+permeation of moisture over projected shelf life in the package (g)+moisture from package fillers (g)

Once the total moisture (g) to be absorbed is calculated, one calculates the desiccant quantity needed as follows:

Quantity of desiccant (g) required =

$$\frac{\text{total moisture to be aborbed by desiccant (g)}}{\text{desiccant capacity at projected storage conditions}}$$
(g water/g desiccant)

The amount of desiccant required may depend upon the number of unit dosage forms to be packaged per container and the water absorptive capacity of the desiccant. This calculation governs the predetermined quantity of desiccant to be provided. Typically, the predetermined desiccant quantity is in excess of the desiccant required. One of ordinary skill in the art will readily appreciate how to use these calculations and determine an appropriate amount of desiccation.

According to a preferred embodiment of the present invention, an appropriate amount of desiccant is employed to absorb moisture from the dosage form. Such a level of desiccation can be achieved using a capsule shell suitable for use in the second embodiment of the present invention, i.e., an HPMC capsule, while such desiccation may not possible for higher moisture content capsules such as gelatin capsules. It is important to note, however, that even in the absence of desiccation, HPMC capsule formulations of the present invention have benefits over similar formulations employing gelatin capsules and over formulations employing no capsules, as demonstrated in FIG. 1 described herein.

A fourth embodiment of the invention is directed to a method of treating an inflammatory condition of the gastrointestinal tract by administering the dosage form of either the first or second embodiment to a patient in need of treatment. Inflammatory conditions of the gastrointestinal tract include, without limitation, ulcerative colitis, irritable bowel syndrome, diverticulitis, and Crohn's disease; the treatment of ulcerative colitis and irritable bowel syndrome by 5-aminosalicylic acid is well known. Dosage forms according to the first or second embodiment of the invention comprise from about 50 mg to about 1,800 mg of 5-aminosalicylic acid. One of ordinary skill in the art could readily employ one or more dosage forms of the present invention to provide a patient in need of treatment with a therapeutically effective dosage of 5-aminosalicylic acid.

A fifth embodiment of the invention is directed to a method of improving the handling properties of a 5-aminosalicylic acid dosage form comprising the steps of: providing at least one tablet containing 5-aminosalicylic acid or a salt thereof as an active ingredient and having an enteric coat; and encapsulating the at least one tablet in a capsule shell. All details with regard to the capsule shell composition, tablet composition, enteric coating composition, etc. are the same as set forth for the first embodiment of the invention A sixth embodiment of the invention is directed to a method of improving the stability of a 5-aminosalicylic acid dosage form comprising the steps of: providing at least one tablet containing 5-aminosalicylic acid or a salt thereof as an active ingredient and having an enteric coat; and encapsulating the at least one tablet in a capsule shell having less than about 10% by weight moisture content at a relative humidity of 60% and a temperature of 25° C. All details with regard to the capsule shell composition, tablet composition, enteric coating composition, etc. are the same as set forth for the second embodiment of the invention.

A seventh embodiment of the invention is directed to a method of modifying the dissolution profile of a dosage form upon storage comprising the step of: providing the dosage form in a kit comprising the dosage form and a predetermined amount of desiccant, wherein the dosage form has (a) a capsule shell having less than about 10% by weight moisture content in the capsule shell at a relative humidity of 60% and a temperature of 25° C. and (b) at least one tablet within the capsule shell, the at least one tablet containing 5-aminosalicylic acid or a salt thereof as an active ingredient and having an enteric coat. All details with regard to the capsule shell composition, tablet composition, enteric coating composition, desiccant amount, etc. are the same as set forth for the second and third embodiments of the invention.

As set forth herein, "dissolution profile" refers to the percentage of 5-aminosalicylic acid dissolved at each of specified sampling intervals, e.g., every 15 minutes, when a dosage form is tested according to the standard protocol for mesalamine delayed-release tablets set forth at pages 3819-3820 of USP 35 Official Monographs. It has been shown that the dissolution profile for certain dosage forms of the present invention exhibits an undesirable delay in the release of active ingredient. Such an effect is shown as a "shift to the right" in the dissolution profile upon storage of the dosage form. As used herein, "modifying the dissolution profile" refers to the prevention or lessening of the right shift in dissolution profile during storage. While 5-aminosalicylic acid formulations are typically stored in the presence of desiccant in order to preserve the stability of those formulations, i.e., in order to prevent the formation of certain known degradants, the present inventors have discovered that the use of a predetermined amount of desiccant (determined as indicated above) has the added benefit of preventing or lessening the right shift of the dissolution profile upon storage. In a preferred embodiment, the dissolution profile of the dosage form upon storage is substantially similar to the dissolution profile of the dosage form upon manufacture. As used herein, "substantially similar" refers to dissolution profiles which have a similarity factor (f2) score of 50-100. One of ordinary skill in the art can readily determine a similarity factor (f2) using the guidance provided in, e.g., Guidance for Industry—Dissolution Testing of Immediate Release Solid Oral Dosage Forms, U.S. Department of Health and Human Services, Food and Drug Administration, Center for Drug Evaluation and Research (CDER), August 1997, BP1. "Storage" is as defined above with regard to the second embodiment of the invention.

The following examples will illustrate the practice of the present invention in some of the preferred embodiments. Other embodiments within the scope of the claims will be apparent to one skilled in the art.

EXAMPLES

Example 1

HPMC Capsule Compared to Gelatin Capsule and Tablet

Tablets were manufactured via wet granulation and compression on a rotary tablet press using the components noted in Table 1 below. The resulting round, concave tablets (approximately 5.5 mm wide and 4.87 mm thick) were then coated with a functional coat (i.e., a first enteric coat) using the components noted in Table 2 according to known methods. Then the tablets were coated with an outer coat (i.e., a second enteric coat) using the components noted in Table 2 below using a conventional coating pan, i.e., solution/suspension is sprayed over a moving bed of tablets and dried in situ.

TABLE 1

Core tablet formulation.

| Ingredient | Concentration (% w/w) | Quantity per tablet (mg) |
| --- | --- | --- |
| Mesalamine, USP | 76.54 | 100.00 |
| Lactose D 20 | 14.62 | 19.10 |
| Povidone | 1.67 | 2.18 |
| Sodium Starch Glycolate | 3.50 | 4.57 |
| Magnesium Stearate | 1.19 | 1.55 |
| Talc USP | 1.99 | 2.60 |
| Colloidal Silicon Dioxide | 0.49 | 0.65 |
| Subtotal | 100.00 | 130.65 |

TABLE 2

Enteric coat formulation.

| Coat | Ingredient | Concentration (% w/w) | Quantity per tablet (mg) |
| --- | --- | --- | --- |
| Functional | Eudragit ®S | 62.90 | 7.34 |
| | Talc | 16.88 | 1.97 |
| | Iron oxide red | 8.23 | 0.96 |
| | Iron oxide yellow | 1.46 | 0.17 |
| | Dibutyl sebacate | 10.54 | 1.23 |
| | Subtotal | 100.00 | 11.67 |
| Outer | Eudragit ®L | 63.22 | 0.55 |
| | Talc | 17.24 | 0.15 |
| | Iron oxide red | 8.05 | 0.07 |
| | Iron oxide yellow | 1.15 | 0.01 |
| | Dibutyl sebacate | 10.34 | 0.09 |
| | Subtotal | 100.00 | 0.87 |
| Polish coating | polyethylene glycol 6000 | 100.00 | 0.2 |
| | Subtotal | 100.00 | 0.2 |

Next four identical tablets were manually loaded into either a gelatin or HPMC capsule. Details of capsules used are shown in Table 3.

TABLE 3

Details of capsules.

| Ingredient | Color | Manufacturer | Capsule Size |
| --- | --- | --- | --- |
| Gelatin | Clear | Capsugel Bornem, Rijksweg 11, Belgium. | 0el |
| HPMC (V cap plus) | Clear | Capsugel Bornem, Rijksweg 11, Belgium. | 0el |

Accelerated stability testing was conducted for tablets made and coated according to Example 1 but not placed in a capsule shell (Batch 1 below). These tablets, as well as dosage forms, with an outer coat and with gelatin or HPMC capsule shell (Batches 2 and 3, respectively), were placed in a 30 ml HDPE bottle sealed with a foil innerseal and child-resistant cap (CRC) (15 tablets or capsules per bottle). Three batches were stored at accelerated stability conditions.

Batch 1 consisted of 100 mg tablets (60 tablets in total per bottle—equivalent to 15×400 mg capsules). Batch 2 consisted of 15 gelatin capsules, each loaded with 4×100 mg tablets. Batch 3 consisted of 15 HPMC capsules, each loaded with 4×100 mg tablets.

Each batch was stored in stability cabinets at accelerated storage conditions—40° C./75% relative humidity—for 17 weeks. At each time point, batches were assayed for the amount of degradant B present according to known methods. Results are shown in Table 4 below and in accompanying FIG. 1.

TABLE 4

Levels of Deg B in each of the batches over time (% w/w).

| Time (weeks) | Batch | | |
| --- | --- | --- | --- |
| | 1 | 2 | 3 |
| 0 | 0 | 0 | 0 |
| 4 | 0.188 | 0.306 | 0.116 |
| 8 | 0.373 | 0.464 | 0.239 |
| 17 | 0.704 | 0.717 | 0.394 |

As can be seen from FIG. 1, dosage forms comprising enterically coated tablets in an HPMC capsule exhibit improved stability as compared to enterically coated tablets and as compared to dosage forms comprising enterically coated tablets contained within a gelatin capsule under accelerated storage conditions.

Example 2

HPMC Capsule

Tablets were manufactured via wet granulation and compression on a rotary tablet press using the components noted in Table 5 below. The resulting capsule-shaped tablets (approximately 14.7 mm×5.9 mm) were then coated with a functional coat (i.e., a first enteric coat) using the components noted in Table 6 below according to known methods using a conventional coating pan, i.e., solution/suspension is sprayed over a moving bed of tablets and dried in situ. Finally coated tablets were manually loaded into a capsule having the composition shown in Table 6.

TABLE 5

Core tablet formulation.

| Ingredient | Quantity per tablet (mg) |
| --- | --- |
| Mesalamine, USP | 400.0 |
| Lactose monohydrate | 76.4 |
| Povidone | 8.7 |
| Sodium Starch Glycolate | 18.3 |
| Magnesium Stearate | 6.2 |
| Talc USP | 10.4 |
| Colloidal Silicon Dioxide | 2.6 |
| Purified water[1] | — |
| Subtotal | 522.6 |

TABLE 6

Enteric coat formulation.

| Coat | Ingredient | % w/w | Mg/tablet |
|---|---|---|---|
| Functional | Methacrylic acid copolymer, type B (Eudragit ®S 12.5[2]) | 2.7 | 17.79 |
| | Talc | 0.7 | 4.74 |
| | Iron oxide red | 0.4 | 2.30 |
| | Iron oxide yellow | 0.1 | 0.42 |
| | Dibutyl sebacate | 0.5 | 3.02 |
| | Acetone[1] | — | — |
| | Water[1] | — | — |
| | Subtotal | 4.4 | 28.27 |
| Polish coating | polyethylene glycol 6000 | 0.1 | 0.57 |
| | Purified water[1] | — | — |
| | Subtotal | 0.1 | 0.57 |
| Capsule | Hydroxypropyl methylcellulose (size 0, Vcaps ® Plus) | 14.8 | 96 |
| | Subtotal | 14.8 | 96 |
| | Total | 100.0 | 647.44 |

[1]processing aid, not present in final product, except in trace amounts
[2]Eudragit ® S 12.5 is an isopropyl alcohol solution containing 12.5% methacrylic acid copolymer, NF Type B ICH stability studies were conducted on a number of batches. The packaging configuration consisted of 12 capsules in a 90 cc bottle with a foil innerseal and child-resistant cap, packed with 7" cotton and with and without desiccant (the amount of dessicant ranged between 0 and 2 g). Samples were stored at accelerated (40° C./75% RH) and long term (25° C./60% RH) storage conditions. Two batches were stored at accelerated and long term storage conditions. Batch A contained 12 HPMC capsules in a 90 cc HDPE bottle with 0 g of desiccant. Batch B contained 12 HPMC capsules in a 90 cc HDPE bottle with 2 g of desiccant. A summary of assay and degradant B levels following storage of samples at 25° C./60% RH conditions is shown in Table 7.

TABLE 7

Summary of Assay and Deg B Levels Following Storage at 25° C. 60% RH.

| | Assay (%) | | Deg B (% w/w) | |
|---|---|---|---|---|
| Batch | T = 0 | T = 6 months | T = 0 | T = 6 months |
| A | 99.9 | 101.9 | 0 | 0.006 (<LOD) |
| B | 99.9 | 101.1 | 0 | 0.006 (<LOD) |

LOD = limit of detection

Testing

Dissolution Profile

Figure 2:
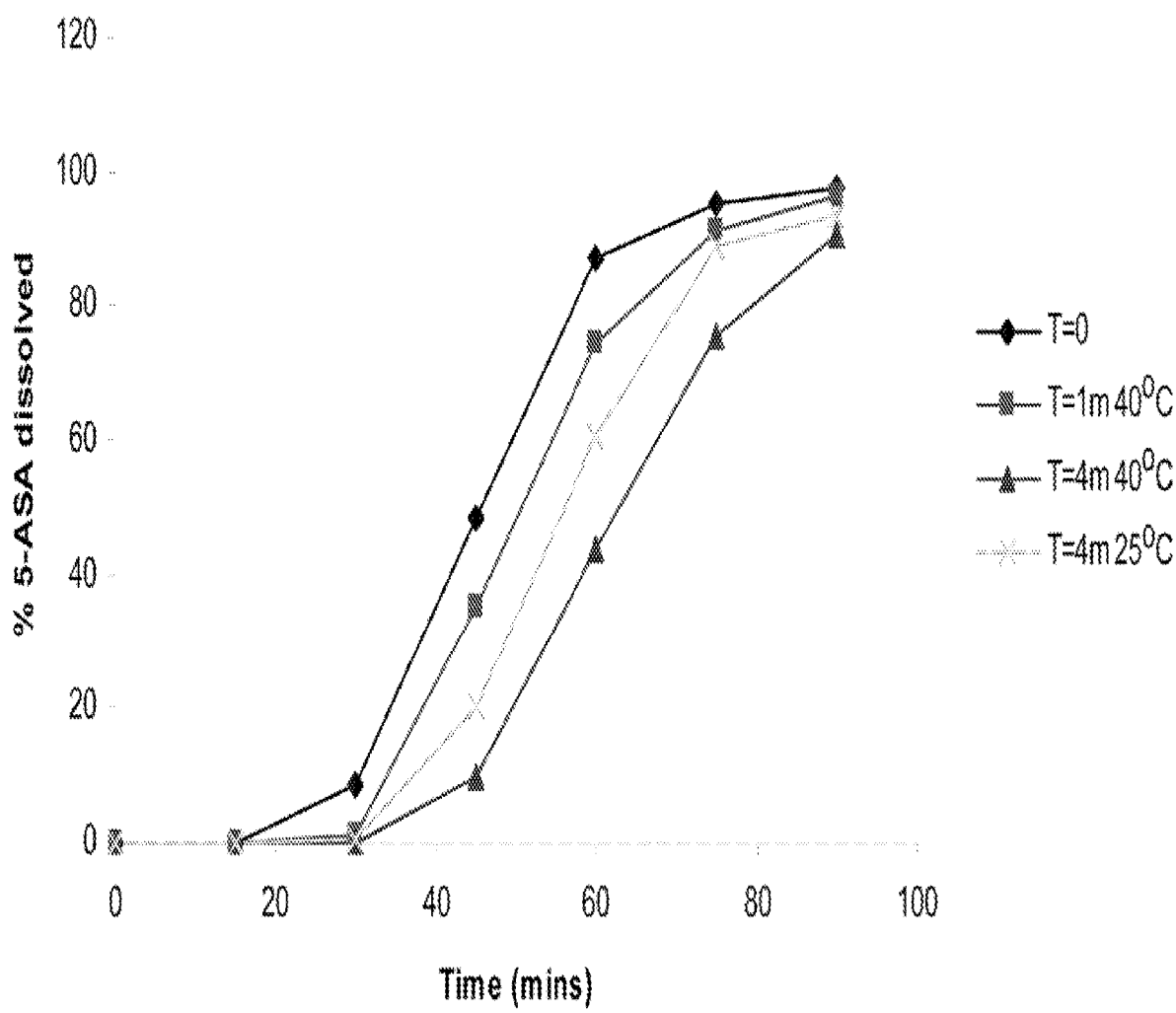
FIG. 2 is a plot of the continuous dissolution profile for HPMC capsule dosage forms according to Example 1 under various conditions.

The dissolution profile of the HPMC capsule dosage form of Example 1 was determined at various times, both at 25° C./60% relative humidity and 40° C./75% relative humidity, when stored with 4 g desiccant (2×2 g StripPax® Multisorb desiccant packets), and the results are shown in FIG. 2 when 180 HPMC capsule dosage forms of Example 1 were placed in a 325 ml bottle packed with 3-4 inches of cotton and sealed with an induction seal. A shift to the right resulting in slower dissolution was seen in the presence of this level of desiccation. Dissolution testing followed the standard protocol for mesalamine delayed-release tablets set forth at pages 3819-3820 of USP 35 Official Monographs.

Figure 3:
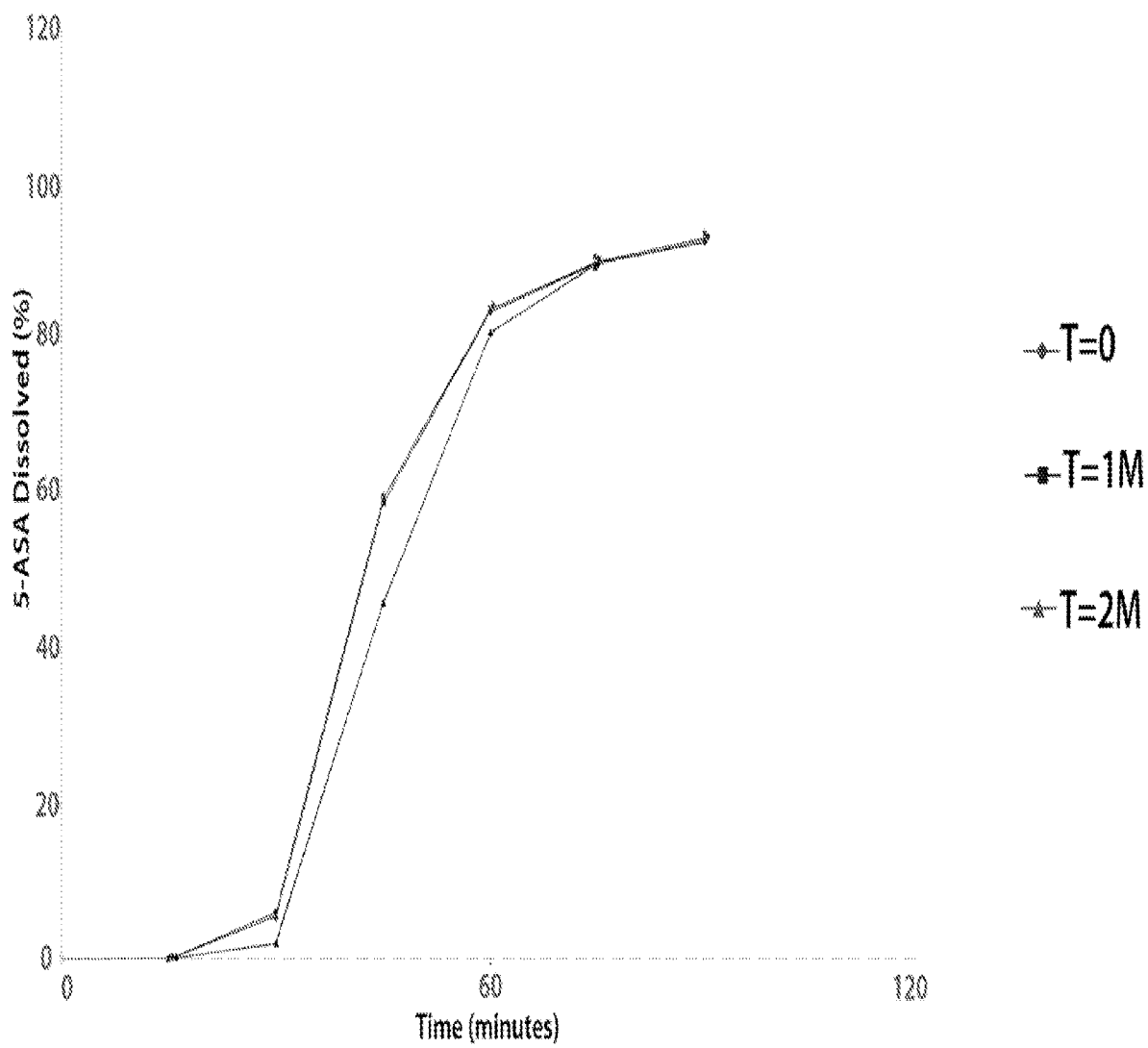
FIG. 3 is a plot of the continuous dissolution profile for HPMC capsule dosage forms according to Example 1 at 40° C./75% relative humidity.

However, when stored with 15 g desiccant (3×5 g Minipax® dessicant) at 40° C./75% relative humidity in the otherwise same packaging configuration, the dissolution profile of the dosage form after both one and two months of storage is remarkably similar to the dissolution profile of the dosage form at time 0 as shown in FIG. 3. In other words, the shift to the right of the dissolution profile seen upon storage with 4 g desiccant is markedly reduced when the dosage form is stored with 15 g desiccant.

Handling

The handling properties of the HPMC capsule dosage form of Example 2 were tested. Specifically, a batch of HPMC capsule dosage forms of Example 2 were friabilated for 15 minutes using a Pharmaceutical Development Copley FR1000 tablet friability tester. The tablets within the capsule dosage forms were then removed and quick tested, i.e., immersed in 0.1N HCl for 120 minutes followed by pH 6.0 buffer for 120 minutes. The same steps, i.e., friabilation and quick test, were performed for tablets having the same composition as those in the capsule dosage form of Example 2. In other words, tablets without the inventive encapsulation were friabilated and then quick tested. Fourteen (14) "early openers" were observed for these tablets which were not contained in a capsule during friabilation. In contrast, only three (3) "early openers" were observed for the tablets contained in the HPMC capsule dosage forms of Example 2. "Early openers" refer to tablets which show signs of compromise of the integrity of the enteric coating, i.e., visible signs of damage to the enteric coating upon observation while submerged in the test medium. These results indicate that encapsulation exerts a positive influence on the handling properties of the tablets.

Numerous alterations, modifications, and variations of the preferred embodiments disclosed herein will be apparent to those skilled in the art, and they are all anticipated and contemplated to be within the spirit and scope of the claimed invention. For example, although specific embodiments have been described in detail, those with skill in the art will understand that the preceding embodiments and variations can be modified to incorporate various types of substitute, additional or alternative materials. Accordingly, even though only few variations of the present invention are described herein, it is to be understood that the practice of such additional modifications and variations and the equivalents thereof, are within the spirit and scope of the invention as defined in the following claims. All patent applications, patents, and other publications cited herein are incorporated by reference in their entirety.

What is claimed is:

1. A dosage form comprising:
    (a) a capsule shell, wherein the capsule shell comprises hydroxypropylmethyl cellulose; and
    (b) at least one tablet within the capsule shell, the at least one tablet containing 5-aminosalicylic acid or a salt thereof as an active ingredient and having an enteric coat that prevents release of the 5-aminosalicylic acid in the upper gastrointestinal tract,
    wherein the at least one tablet is a monolithic tablet, wherein the capsule shell has less than about 10% by weight moisture content at a relative humidity of 60% and a temperature of 25° C., wherein the dosage form has improved handling properties such that a percentage of early openers following friabilation and quick testing is lower for the at least one tablet within the capsule shell as compared to the at least one tablet without a capsule shell, wherein no more than 0.15% w/w 5-[2-formyl-5-(hydroxymethyl-1H-pyrrol-1-yl]-2-hydroxybenzoic acid accumulates upon storage of the dosage form at a relative humidity of 60% and a temperature of 25° C. for a period of at least six months, and wherein the moisture content of the capsule shell is greater than a moisture content of the at least one tablet.

2. The dosage form according to claim 1, wherein the at least one tablet comprises a reducing sugar.

3. The dosage form according to claim 1, wherein the capsule shell contains one, two, three, four or five tablets.

4. The dosage form according to claims 3, wherein the capsule shell contains one tablet.

5. The dosage form according to claim 1, wherein the at least one tablet contains from about 50 mg to about 1,800 mg of 5-aminosalicylic acid.

6. The dosage form according to claim 1, wherein the enteric coat comprises a material capable of delivering the 5-aminosalicylic acid to the colon of a human.

7. The dosage form according to claim 1, wherein the enteric coat comprises a material selected from the group consisting of poly(methacrylic acid, methyl methacrylate) 1:2, poly(methacrylic acid, methyl methacrylate) 1:1, and mixtures thereof.

8. The dosage form according to claim 1, wherein the enteric coat further comprises a plasticizer.

9. The dosage form according to claim 8, wherein the plasticizer is selected from the group consisting of polyethylene glycols, propylene glycols, 1,2-propylene glycol, dibutyl phthalate, dibutyl sebacate, diethyl phthalate, tributyl citrate, triethyl citrate, tributyrin, butyl phthalyl butyl glycolate, triacetin, castor oil, citric acid esters, and combinations thereof.

10. The dosage form according to claim 1, wherein the enteric coat further comprises inert solid particulates.

11. The dosage form according to claim 1, wherein the enteric coat comprises a single enteric coating.

12. The dosage form according to claim 1, wherein the enteric coat comprises a plurality of enteric coatings.

13. The dosage form according to claim 1, wherein the total thickness of the enteric coat ranges from about 50 µm to about 250 µm.

14. The dosage form according to claim 1, wherein the enteric coat comprises an inner layer of a first polyacrylic acid copolymer enteric coating and an outer layer of a polyacrylic acid copolymer enteric coating that is different than the inner layer.

15. The dosage form according to claim 14, wherein the inner layer of enteric coating is poly(methacrylic acid, methyl methacrylate) 1:2 and the outer layer of enteric coating is poly(methacrylic acid, methyl methacrylate) 1:1.

16. The dosage form according to claim 1, wherein the capsule does not have an enteric coating.

17. The dosage form according to claim 1, wherein the at least one tablet is greater than 5 mm in diameter.

18. A method of treating an inflammatory condition of the lower gastrointestinal tract comprising administering a dosage form according to claim 1 to a patient in need of treatment.

* * * * *